United States Patent
Nishiyama et al.

(10) Patent No.: US 8,093,557 B2
(45) Date of Patent: Jan. 10, 2012

(54) METHOD AND APPARATUS FOR REVIEWING DEFECTS

(75) Inventors: Hidetoshi Nishiyama, Hitachinaka (JP);
Toshifumi Honda, Yokohama (JP);
Sachio Uto, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 141 days.

(21) Appl. No.: 12/573,479

(22) Filed: Oct. 5, 2009

(65) Prior Publication Data

US 2010/0019150 A1    Jan. 28, 2010

Related U.S. Application Data

(63) Continuation of application No. 11/668,510, filed on Jan. 30, 2007, now Pat. No. 7,601,954.

(30) Foreign Application Priority Data

Mar. 3, 2006  (JP) .................................. 2006-057471

(51) Int. Cl.
*G01N 23/00* (2006.01)
(52) U.S. Cl. ..................................... 250/310; 356/237.4
(58) Field of Classification Search .................. 250/306, 250/307, 310; 356/237.4, 237.2
See application file for complete search history.

(56) References Cited

U.S. PATENT DOCUMENTS

| 5,734,164 | A | 3/1998 | Sanford |
| 7,075,077 | B2 | 7/2006 | Okuda |
| 7,269,280 | B2 | 9/2007 | Hiroi |
| 7,423,746 | B2 * | 9/2008 | Takeda et al. ............... 356/237.4 |
| 7,851,753 | B2 * | 12/2010 | Uto et al. ....................... 250/310 |

FOREIGN PATENT DOCUMENTS

| JP | 05-041194 | 2/1993 |
| JP | 2001-133417 | 5/2001 |
| JP | 2003-007243 | 1/2003 |
| JP | 2005-156537 | 6/2005 |

* cited by examiner

*Primary Examiner* — Kiet Nguyen
(74) *Attorney, Agent, or Firm* — Antonelli, Terry, Stout & Kraus, LLP.

(57) ABSTRACT

A method of inspecting defects of a sample includes a first step for, on a basis of position information of defects on a sample placed on a movable table which is previously detected and obtained by an other inspection system, driving the table so that the defects come into a viewing field of an optical microscope having a focus which is adjusted, a second step for re-detecting the defects to obtain a first detection result, a third step for correcting the position information of defects on a basis of position information of defects re-detected of the first detection result, and a fourth step for reviewing the defects whose position information is corrected to obtain a second detection result. The method includes classifying types of defects on basis of the first detection result and the second detection result.

7 Claims, 10 Drawing Sheets

*FIG. 3A*　　*FIG. 3B*
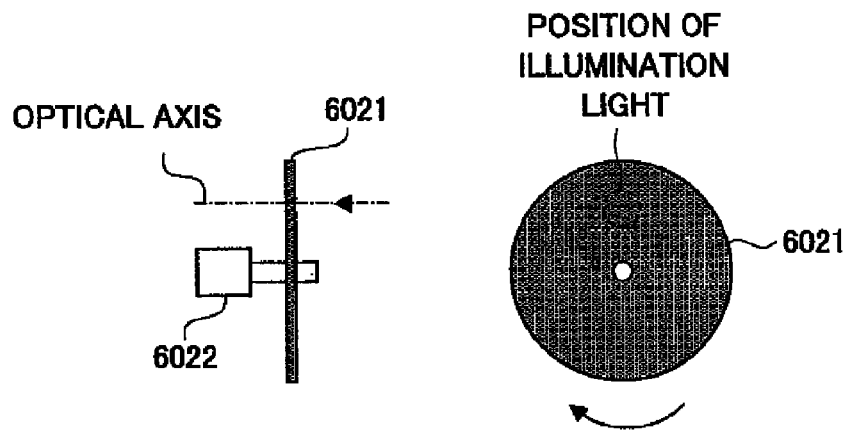
*FIG. 4*
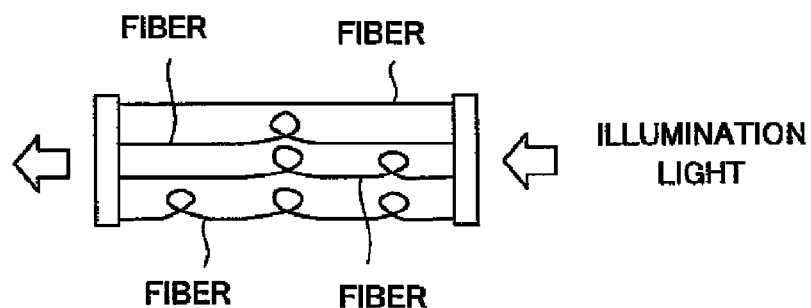
*FIG. 5*
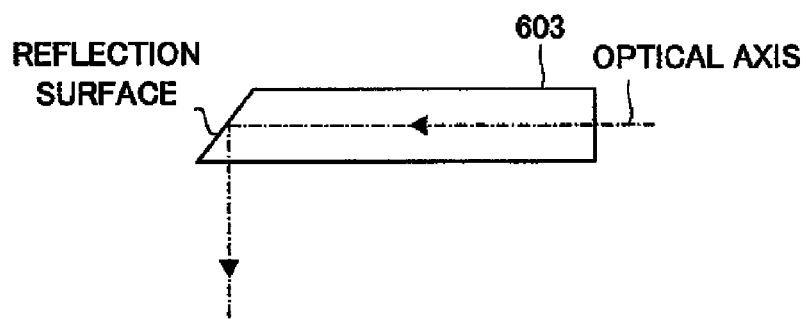

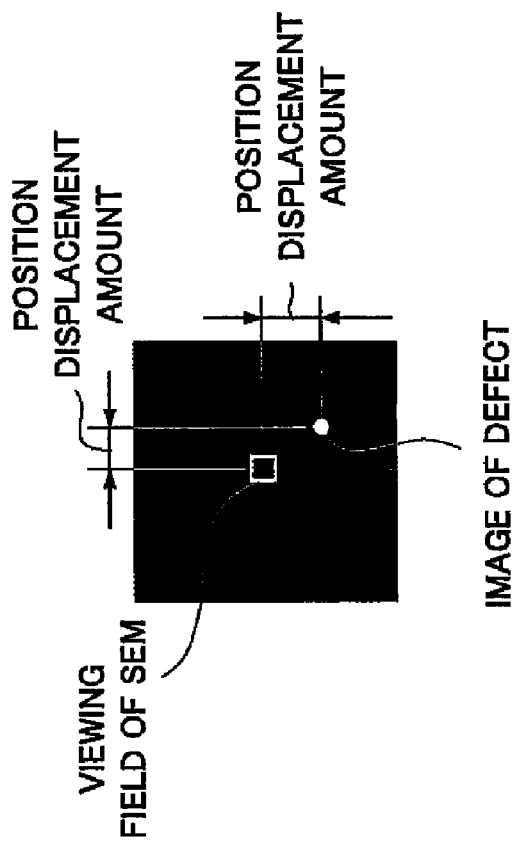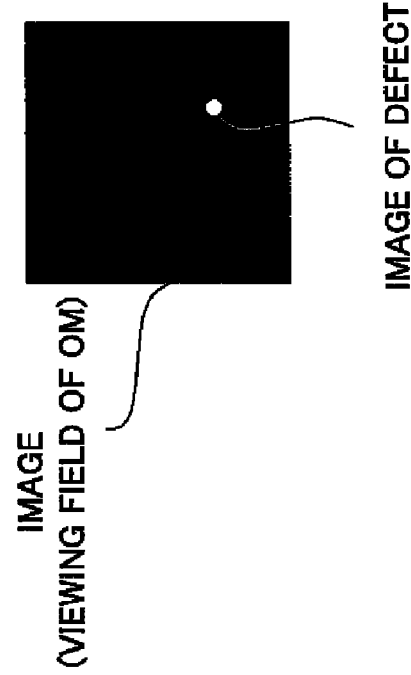

|  |  | SEM DETECTION RESULT | |
|---|---|---|---|
|  |  | DETECTION POSSIBLE | DETECTION IMPOSSIBLE |
| OM DETECTION RESULT | DETECTION POSSIBLE | SURFACE DEFECT | UNDER FILM DEFECT |
|  | DETECTION IMPOSSIBLE | — | NUISANCE |

METHOD AND APPARATUS FOR REVIEWING DEFECTS

CROSS-REFERENCE TO RELATED APPLICATION

This application is a continuation of U.S. application Ser. No. 11/668,510, filed Jan. 30, 2007 now U.S. Pat. No. 7,601,954, the contents of which are incorporated herein by reference.

The present application claims priority from Japanese Patent Application No. JP 2006-057471 filed on Mar. 3, 2006, the content of which is hereby incorporated by reference into this application.

TECHNICAL FIELD OF THE INVENTION

The present invention relates to a defect reviewing technique for reviewing defects occurring in semiconductor manufacturing processes. More particularly, a technique effectively applied to a method and an apparatus for reviewing defects using an electron microscope and an X-ray analyzer and the like.

BACKGROUND OF THE INVENTION

For example, in semiconductor manufacturing processes, existence of foreign matters (particles) or defects (hereinafter, referred to as defects, which include foreign matters and pattern defects) on a semiconductor substrate (wafer) causes incomplete insulation between wires and other failures such as short-circuit and the like. Further, along with miniaturization of circuit patterns, finer defects cause incomplete insulation of capacitors and destruction of gate oxide films. These defects come from various causes including ones occurring from moving parts of a transportation apparatuses, ones emitted from human bodies, ones generated by reaction of process gas in processing apparatuses, ones mixed in chemicals and materials, and others, and are mixed in various states. Accordingly, it is necessary to detect defects occurring in the manufacturing processes, pinpoint the occurring source of defects, and prevent defects from being outflowing.

In the prior art, as the method for finding out the causes of defects, a method has been employed where the defect position is first identified by a defect inspection system, and the defect concerned is reviewed in detail by use of a SEM (Scanning Electron Microscope) and the like and classified, and compared with the database and the cause of the defect is estimated.

Herein, the defect inspection system includes: an optical particle inspection system that implements dark-field illumination on the surface of a semiconductor substrate by a laser beam, detects scattering light from a defect, and identifies the defect position; and an optical visual inspection system or a SEM inspection system with a lamp light or a laser beam or an electron ray as its illumination light, which detects a light-field optical image of a semiconductor substrate, compares this with reference information and thereby identifies the defect position on semiconductor substrate.

These reviewing methods are disclosed in Japanese Patent Application Laid-Open Publication No. 2001-133417, Japanese Patent Application Laid-Open Publication No. 2003-7243, Japanese Patent Application Laid-Open Publication No. 5-41194, and Japanese Patent Application Laid-Open Publication No. 2005-156537.

Meanwhile, when a defect of the semiconductor substrate is to be detected by use of the optical particle inspection system, in order to increase the throughput of the inspection, the semiconductor substrate is scanned by a laser beam of a large spot size for detection. For this reason, the precision of the detect position obtained from the spot position of the laser beam that scans the semiconductor substrate will include large error components.

When a defect is reviewed in detail by the SEM on the basis of the position information of the defect including such error components, there is a case where reviewing is made with a further higher magnification (=small viewing field) than the magnification of the optical system of the optical particle inspection system, and accordingly, the defect to be reviewed may not come into the viewing field of the SEM. In order to make the detect of the reviewed object come into the viewing field of the SEM, the detect is searched for while the viewing field of the SEM is moved, but the viewing field is small, therefore, it takes much time. And consequently, the throughput of the SEM reviewing declines, and it take much time to analyze the defect, which is a problem.

In order to solve the above problem, in the Japanese Patent Application Laid-Open Publication No. 2001-133417, Japanese Patent Application Laid-Open Publication No. 2003-7243, Japanese Patent Application Laid-Open Publication No. 5-41194, and Japanese Patent Application Laid-Open Publication No. 2005-156537 mentioned previously a parallel arrangement of the SEM and an optical microscope is disclosed. However, in order to detect defects precisely by the optical microscope, it is necessary to focus the optical microscope, but when a stage is employed so as to move up and down the semiconductor substrate for focusing, a movement stage in the vertical direction is additionally arranged to a stage that can move in the horizontal direction at a high speed and with high precision, the apparatus will become expensive and massive, which is another problem.

SUMMARY OF THE INVENTION

The present invention provides, according to a method and an apparatus for reviewing defects in detail by a SEM where the reviewed defects are detected by an optical particle inspection system or an optical visual inspection system, the method and apparatus capable of making a defect of a reviewed object come into the viewing field of the SEM or the like, and making the apparatus scale compact.

The above and other novel characteristics of the present invention will be apparent from the description of this specification and the accompanying drawings.

The typical ones of the inventions disclosed in this application will be briefly described as follows.

In the present invention, there is provided a method for reviewing defects of a sample, including the following steps. A first step for, on the basis of position information of defects on the sample placed on a table that can move in an X-Y plane, the position information of defects being detected and obtained by inspecting the sample by other inspection system beforehand, driving the table and making the defects come into the viewing field of an optical microscope, and adjusting the focus of the optical microscope onto the sample; a second step for re-detecting the defects by the optical microscope; a third step for correcting the position information of defects on the basis of the position information of defects re-detected at the second step; and a fourth step for reviewing the defects whose position information is corrected at the third step by an electron microscope. At the first step, adjusting the focus of the optical microscope onto the sample is made by moving a part of or whole of the optical microscope in the normal line direction of the sample surface.

Further, in the present invention, there is provided a method for reviewing defects of a sample, including the following steps. A step for, by use of an image obtained by light-field illuminating on a sample placed on a table that can move in an X-Y plane and photographing the sample by an optical microscope, adjusting and aligning the position and rotation direction of the sample in the X-Y plane; a step for, on the basis of position information of defects on the sample aligned, wherein the position information of defects is detected and obtained by inspecting the sample by other inspection system beforehand, driving the table and making the defects come into the viewing field of the optical microscope, and adjusting the focus of the optical microscope onto the sample; a step for dark-field illuminating on the defects and re-detecting the defects by use of the optical microscope with the adjusted focus to obtain the position information of the defects in the X-Y plane; a step for correcting the position information of defects detected and obtained by inspecting the sample by the other inspection system beforehand on the basis of the position information of the re-detected defects in the X-Y plane; and a step for driving the table so as to make the defects of the sample whose position information is corrected come into the viewing field of an electron microscope, and reviewing the defects by an electron microscope. In addition, in the step for adjusting the focus of the optical microscope onto the sample, adjusting the focus of the optical microscope onto the sample is made by moving a part of or whole of the optical microscope in the normal line direction of the sample surface.

Furthermore, according to the present invention, there is provided an apparatus for reviewing defects of a sample, including the following means. An optical microscope means that, by use of a position information of defects on a sample detected by other defect inspection system beforehand, re-detects the defects and has a light-field illumination optical system and a dark-field illumination optical system, a table means that loads the sample and can move on an X-Y plane, focus position adjusting means that adjusts the focus position of the optical microscope onto the sample placed on the table means, position information correcting means that corrects position information of defects detected by the other defect inspection system beforehand on the basis of the position information of defects on the sample redetected by the optical microscope whose focus position is corrected by the focus position adjusting means, and electronic microscope means that reviews the defects whose position information is corrected by the position information correcting means on the sample transferred by the table means. The focus position adjusting means adjusts the focus position of the optical microscope onto the sample placed on the table means by moving a part of or whole of the optical microscope in the normal line direction of the sample surface.

The effects obtained by typical aspects of the present invention will be briefly described below.

According to the present invention, when defects detected by the optical defect inspection system is reviewed in detail by the SEM or the like, it is possible to make defects of reviewed objects come precisely into the viewing field of the SEM or the like, and accordingly, it is possible to increase the throughput of the detailed inspection of defects using the SEM or the like. Further, it is possible to reduce the scale of the stage to load samples to be inspected, and consequently, it is possible to make the apparatus inexpensive and compact.

These and other objects, features and advantages of the invention will be apparent from the following more particular description of preferred embodiments of the invention, as illustrated in the accompanying drawings.

BRIEF DESCRIPTIONS OF THE DRAWINGS

FIG. 3A is a detail side view showing a coherency reducing unit in the first embodiment of the present invention;

FIG. 3B is a detail front view showing the coherency reducing unit in the first embodiment of the present invention;

FIG. 4 is a detail view showing another example of a coherency reducing unit in the first embodiment of the present invention;

FIG. 5 is a detail view showing an epi-mirror in the first embodiment of the present invention;

FIG. 8A is a view showing an image acquired by the dark-field detection method of the optical microscope in the first embodiment of the present invention;

FIG. 8B is a view showing a defect displacement calculation image on the basis of an image acquired by the dark-field detection method of the optical microscope in the first embodiment of the present invention;

DESCRIPTIONS OF THE PREFERRED EMBODIMENTS

Hereinafter, embodiments of the present invention will be described in detail with reference to the accompanying drawings. Note that components having the same function are denoted by the same reference symbols throughout the drawings for describing the embodiment, and the repetitive description thereof will be omitted.

First Embodiment

With reference to FIG. 1 to FIG. 13, a defect reviewing method and an example of an apparatus thereof according to a first embodiment of the present invention are explained hereinafter.

Figure 1:
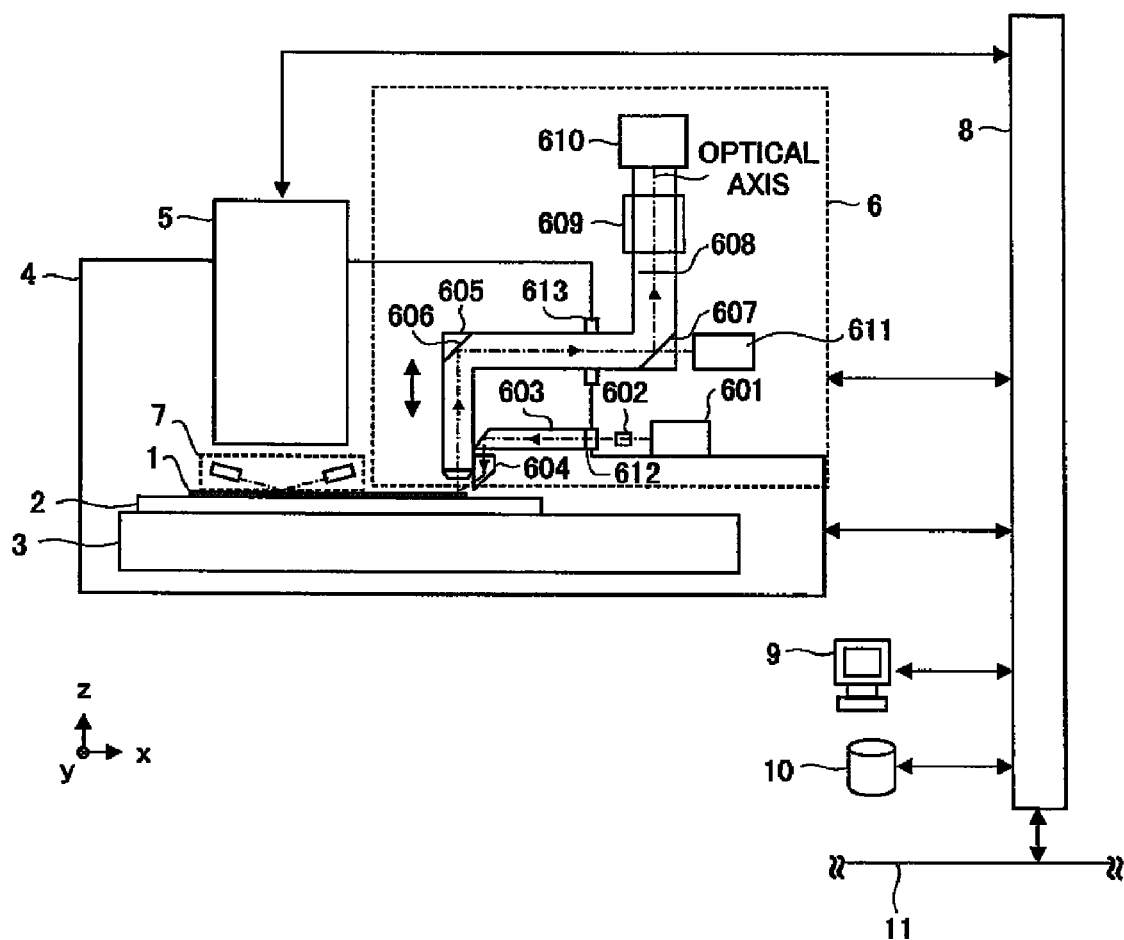
FIG. 1 is a view showing an example of a structure of a defect reviewing apparatus according to a first embodiment of the present invention.

FIG. 1 is a view showing an example of the structure of a defect reviewing apparatus according to the first embodiment of the present invention. The defect reviewing apparatus according to the present embodiment is an apparatus for reviewing defects occurring in manufacturing processes, in device manufacturing processes where circuit patterns are formed on a substrate such as a semiconductor device and the like, and is structured of a sample 1 to be inspected, a sample holder 2 that holds the sample 1, a stage 3 that can move the sample holder 2 and move the entire surface of the sample 1 to the portion under a microscope, a vacuum chamber 4, a scanning electron microscope (hereinafter referred to as SEM) 5, an optical microscope (hereinafter referred to as OM) 6, height detecting system 7, a control system 8, a user interface 9, a data base 10, and a network 11 for connecting to a host system.

Further, the OM 6 comprising a dark-field illuminating unit 601, a coherency reducing unit 602, an epi-mirror 603, an integrated rhombic mirror 604, a detection optical system 605, a mirror 606, a half mirror 607, an optical filter 608, a zoom lens 609, a detector 610, a light-field illuminating unit 611, a vacuum shutout glass 612, a Z-movement mechanism (including bellows) 613, and lenses not illustrated therein. Furthermore, the stage 3, the vacuum chamber 4, the SEM 5, the OM 6, the height detecting system 7, the user interface 9, the data base 10, and the network 11 are connected to the control system 8.

In the defect reviewing apparatus structured as above, especially, the OM 6 has a function to re-detects (hereinafter referred to also as detects) the position of defects on the sample 1 detected by an optical defect inspection system, and the Z-movement mechanism 613 and the height detecting system 7 and the like have a function as focusing means arranged on the OM 6 for focusing on the sample 1, and the control system 8 and the like has a function as position correcting means for correcting position information of defects on the basis of position information of defects re-detected by the OM 6, and the SEM 5 has a function to review defects whose position information is corrected by the control system 8 and the like, and the structure is so made that when focusing is carried out in the OM 6, the illumination position and detection position of the OM 6 are not changed to the sample 1.

Hereinafter, details of the respective units are explained with reference to FIG. 2 to FIG. 13.

Figure 2:
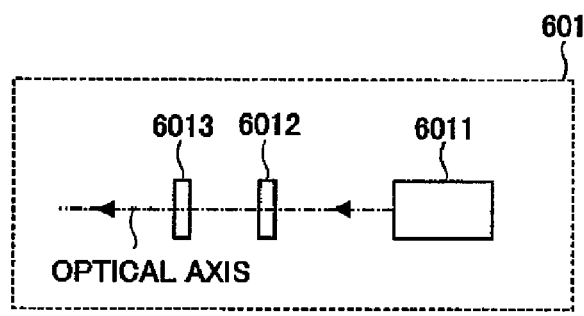
FIG. 2 is a detail view showing a dark-field illuminating unit in the first embodiment of the present invention.

FIG. 2 shows details of the dark-field illuminating unit 601. The dark-field illuminating unit 601 comprises an illumination light source 6011, a wavelength plate 6012 which adjusts the polarization direction of illumination light, and a shutter 6013 which controls ON/OFF of radiation of illumination light.

The illumination light source 6011 is a laser oscillator or a lamp house. The laser oscillator can use visible laser of wavelength 532 nm and 488 nm, 405 nm and the like, ultraviolet laser of wavelength 355 nm and the like, deep ultraviolet laser of wavelength 266 nm and 199 nm and the like, and multiple wavelength laser, and either continuous oscillation laser or pulse oscillation laser can be used. Further, as lamp light, Hg lamp and Xe lamp may be used. With regard to the selection method of these, the visible laser and the lamp can realize a stable and inexpensive apparatus, meanwhile the short wavelength laser can realize an apparatus with a high defect detecting sensitivity.

Next, the coherency reducing unit 602 is used to reduce the coherency of laser and the like and stabilize detected signals. The function of this coherency reducing unit 602 is to reduce spatial coherency and time coherency, and one example is shown in FIG. 3. FIG. 3A is a side view of the coherency reducing unit 602, and FIG. 3B is a front view thereof. The coherency reducing unit 602 comprises a scattering plate 6021, and a rotation motor 6022 for the scattering plate. The scattering plate 6021 rotates around the motor shaft of the rotation motor 6022. When light emitted from the dark-field illuminating unit 601 goes through the scattering plate 6021, it is possible to reduce coherency. Meanwhile, although the example with the scattering plate is shown in the present embodiment, other means may be employed as long as it changes light phases spatially per hour. And as shown in FIG. 4, a means where fibers with different lengths are bundled and thereby changing phases of light emitted from respective fibers may be employed.

The epi-mirror 603, as shown in FIG. 5, has a function to reflect incoming light to the Z-axis direction. Further, the integrated rhombic mirror 604 is a mirror that collects the light going out from the epi-mirror 603 to the focus position of the detection optical system 605, and is arranged in the detection optical system 605. This may be a prism instead of a mirror.

The detection optical system 605 comprises a plurality of lenses, and has a function to collect lights reflected and scattered from the sample 1 and provide an image on the detector 610 via the optical filter 608 and the zoom lens 609. Herein, it is preferable that lights coming into the optical filter 608 are parallel. An advantage of parallel lights is that there is no change of light path length made by the optical filter 608.

The optical filter 608 is a filter that modulates light, and is for example a polarization plate. However, when an optical filter is not used, a glass plate may be employed instead of a movement mechanism not illustrated therein.

Next, details of the zoom lens 609 are explained hereinafter. A function of the zoom lens 609 is to change the image formation magnifications of the OM 6. The change of the image formation magnifications is used at alignment. For example, the sample 1 held by the sample holder 2 often has displacement in the rotation direction or the X-Y plane direction. Accordingly, it is needed to align the sample 1, but since the displacement amount at the first time when the sample 1 is placed is large, in order to search for texture for alignment, it is necessary to search for it in a wide viewing filed. On the other hand, highly precise positioning is necessary for defect reviewing, and highly precise alignment is required accordingly, and alignment by high magnification reviewing is required. At this moment, the viewing field becomes small, therefore it is preferable to have multiple magnifications.

Figure 6:
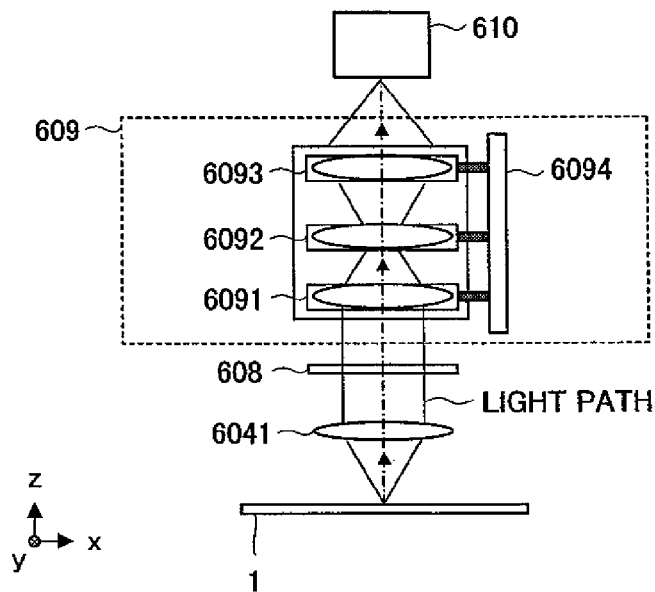
FIG. 6 is a detail view showing a zoom lens in the first embodiment of the present invention.

As shown in FIG. 6, the zoom lens 609 comprises lenses 6091, 6092, 6093, and a movement mechanism 6094 that moves the respective lenses in the Z-direction. In the present embodiment, in order to change magnifications without changing the distance between the sample 1 and the detector 610, the distances among the lenses 6091, 6092, 6093 are changed, and thereby changing magnifications.

The detector 610 is, for example, a two-dimensional CCD camera. As its performance, it may have sensitivity to the wavelength of illumination light source of the light-field illuminating unit 6011, and may have a TDI (Time Delay Integration) function, and a CCD unit of rear surface radiation type may be employed too. In the case having the TDI function, highly sensitive detection of fine light is feasible, therefore it is advantageous with a small illumination light amount, meanwhile the advantage of using the CCD of rear surface radiation type is that highly sensitive detection is feasible in wavelength ranges of ultraviolet ray and deep ultraviolet ray. Further, in the case of a structure where the sample 1 is scanned by illumination light at photographing, a one-dimensional CCD sensor may be employed. Further, a color camera may also be employed. An advantage in using a color camera is that color images of the sample 1 can be obtained, and defects can be identified from color information of the sample 1.

Figure 7:
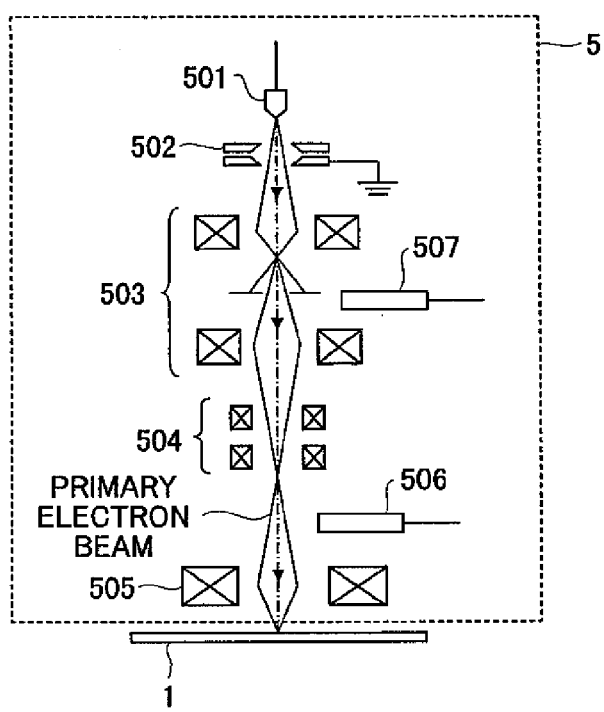
FIG. 7 is a detail view showing an electron microscope in the first embodiment of the present invention.

The SEM 5 is described with reference to FIG. 7. The SEM 5 comprises an electron source 501 that generates primary electron, an acceleration electrode 502 that accelerates the primary electron, a focusing lens 503, a deflector 504 that deflects the primary electron for two-dimensional scanning, an objective lens 505 that focuses the primary electron onto the sample 1, a secondary electron detector 506 that detects secondary electron generated from the sample 1, and a reflection electron detector 507 that detects reflection electron generated from the sample 1. Meanwhile, two or more of the detectors 506 and 507 respectively may be arranged.

Operations in the structure of the defect reviewing apparatus shown in FIG. 1 are explained hereinafter. First, the sample 1 is transferred onto the sample holder 2 in the vacuum chamber 4 via a load lock chamber not illustrated. Then, the sample 1 is moved to the viewing field position of the OM 6 by control of the stage 3. At this moment, there is a possibility that the sample 1 is displaced from the focus position of the OM 6. When the height of the sample 1 is displaced from the focus position, the detection optical system 605 is moved in Z-direction by use of the Z-movement mechanism 613 so that the sample is set onto the focus position of the OM 6. At this moment, since the integrated rhombic mirror 604, the mirror 606, the half mirror 607, the optical filter 608, the zoom lens 609, and the detector 610 are arranged in the detection optical system 605, they move together with the detection optical system 605. Meanwhile, the method to determine the movement amount in the Z-direction is described later.

After the Z-position of the detection optical system 605 is adjusted, alignment of the sample 1 is performed. The alignment is mainly for correcting the parallel movement amount and rotation amount of the sample 1 in the X-Y plane, and aligning the coordinate system of an inspection system and the coordinate system of the defect reviewing apparatus according to the present embodiment. As the method of alignment, the image of the sample 1 is acquired by the OM 6, and the acquired image is processed and the position to be referred is calculated. At this moment, in the case of a sample where circuit patterns are not formed, alignment is made with the edge portion of the outline of the sample 1, and in the case of a sample where circuit patterns are formed, image processing is performed with circuit pattern existing at a predetermined position.

The alignment is carried out by use of the image acquired by light-field detection method. In the light-field detection, illumination light is emitted from the light-field illuminating unit 611, and reflected by the mirror 606 and the half mirror 607, and radiated onto the sample 1. The reflection light from the sample 1 is reflected by the mirror 606 and the half mirror 607, and provide an image on the detector 610 by the zoom lens 609. Herein, the light-field illuminating unit 611 is, for example, a lamp illumination. In addition, in the light-field detection according to the present embodiment, the optical filter 608 is changed with a glass plate of the same thickness by use of a movement mechanism not illustrated. When the alignment is carried out with the edge of the outline of the sample 1, several images of the positioning point (notch or orientation flat in the case when the sample 1 is a wafer) of the sample 1 and profile are acquired and the process is carried out.

After the alignment, according to the position information of the defects outputted from the defect inspection system, the defect position is moved to the viewing field position of the OM 6, and images of defects are acquired by the dark-field detection method of the OM 6. At this moment, when the height of the sample 1 at each defect position is displaced from the focus position of the OM 6, focusing is carried out by the method mentioned above.

Here, the dark-field detection method is explained. The dark-field detection method is applied mainly to a sample where circuit patterns are not formed. At the dark-field detection, first, illumination light is emitted from the dark-field illuminating unit 601. The illumination light may be either laser light or lamp light, but illumination can be made brighter with the laser light, therefore it is preferable to employ the laser light. However, in the case of a sample 1 on which a film of a high reflection ratio such as an aluminum film is applied, the illumination may be low, therefore the lamp light may be employed.

The coherency of the light emitted from the dark-field illuminating unit 601 is reduced by the coherency reducing unit 602. This is mainly for reducing speckle of laser light, and it may be omitted in the case to use lamp light. The light passing the coherency reducing unit 602 goes through the vacuum shutout glass 612, and goes into the vacuum chamber 4, and is bent to the Z-direction by the epi-mirror 603. The light reflected by the epi-mirror 603 is radiated onto the sample 1 at the focus position of the detection optical system 605 by the integrated rhombic mirror 604. Light reflected and scattered from the sample 1 are collected by the lens of the detection optical system 605, and reflected by the mirror 606 and the half mirror 607, and goes into the optical filter 608. The light passing the optical filter 608 goes through the zoom lens 609 and an image is provided at the photographing position of the detector 610, and is converted into digital signals by the detector 610, and sent to the control system 8.

The images acquired by the dark-field detection method of the OM 6 are stored into the control system 8 as a gray image or a color image as shown in FIG. 8A. The control system 8 calculates the viewing field area of the SEM 5 and the displacement amount of the defect position as shown in FIG. 8B, and registers the displacement amount as a coordinate correction value. With regard to the method of calculating the displacement amount, for example, with the center of viewing field of the SEM 5 as the center of the image, the number of pixels between the coordinate of center of gravity of defect position in the image and the center of the image is calculated, and the number of pixels is multiplied by the dimension of the pixel image. Thereafter, the sample 1 is moved by the stage 3 so that the defect comes in the viewing field area of the SEM 5 by use of the coordinate correction value, and the defect is reviewed by the SEM 5. The reviewed defect image is sent to the control system 8, and used for display to the user interface 9 or registration to the database 10, or automatic defect classification process or the like.

Next, operations of the SEM 5 are described with reference to FIG. 7. Primary electron emitted from the electron source 501 is accelerated to a desired speed by the acceleration electrode 502, and by the focusing lens 503 and the objective lens 505, converged onto the sample 1. From the sample 1, secondary electron and reflection electron triggered by the primary electron are emitted. The emitted electron is detected by the secondary electron detector 506 and the reflection electron detector 507, and converted into digital signals by a photoelectric converter and an A/D converter not illustrated therein. The primary electron is deflected by the deflector 504, and the two-dimensional area on the sample 1 is scanned, and the signal of the area is obtained. The obtained signal is digitalized, and sent to the control system 8, and designed as an image therein. Meanwhile, the focus position of the SEM 5 may be adjusted at each position, or the Z-position information calculated at reviewing of the OM 6 may be stored, and the focus position for reviewing by the SEM 5 may be calculated and used.

Figure 9:
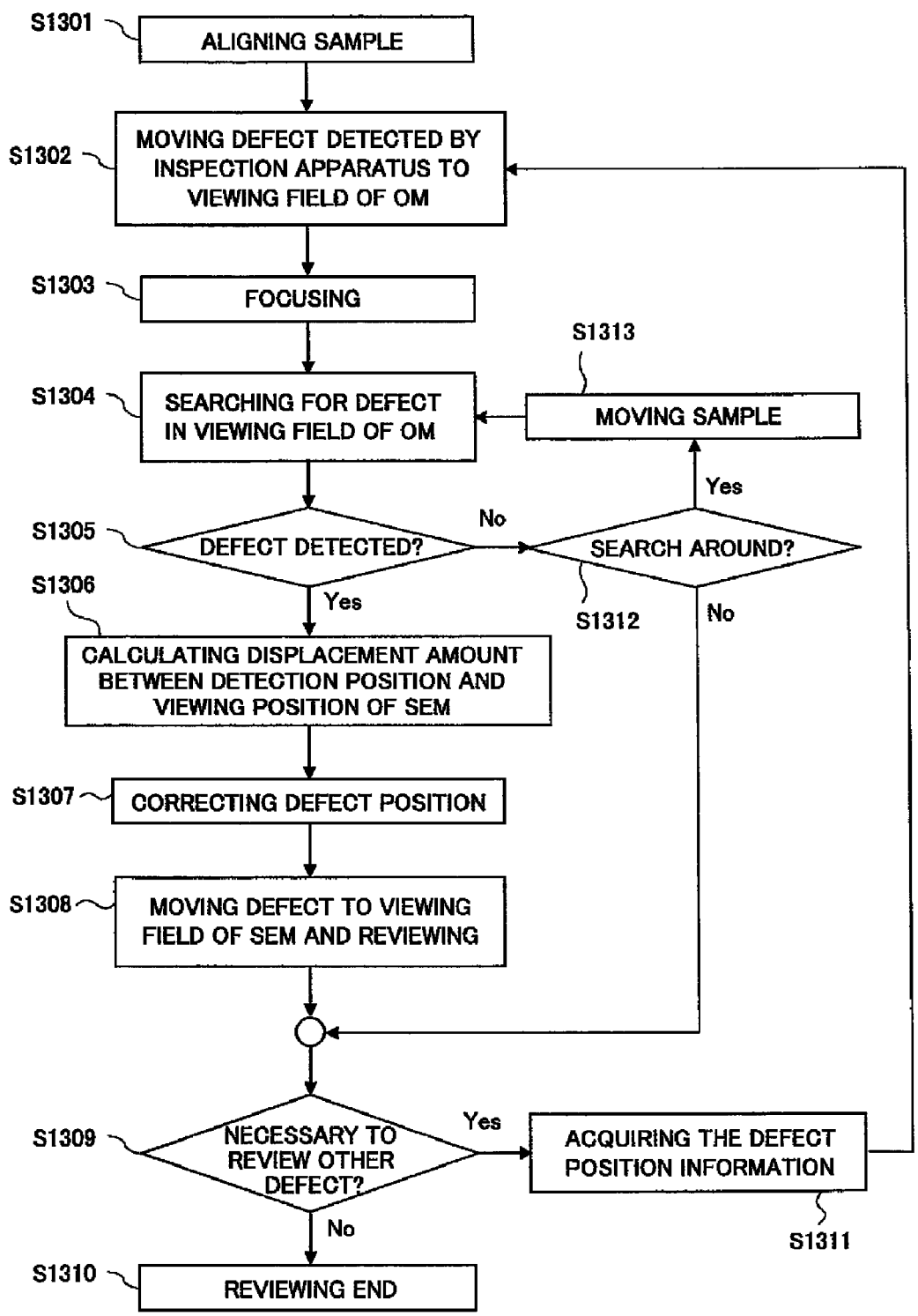
FIG. 9 is a view showing a defect reviewing sequence in the first embodiment of the present invention.

The flow of the defect reviewing is explained with reference to FIG. 9. First, the sample 1 is aligned (S1301). This is the alignment by the OM 6 as mentioned previously. Next, according to the position information of the defect detected by the defect inspection system, the defect to be reviewed on the sample 1 is moved to the viewing field of the OM 6 (S1302). The OM 6 is moved and focusing is performed (S1303). The defect position is searched in the image acquired by the OM 6 (S1304), and if the defect is detected (S1305-Yes), the displacement amount between the defect detected position detected by the OM 6 and the viewing field position of the SEM 5 is calculated (S1306). On the basis of the displacement amount, the position information of the defect is corrected (S1307), and the corrected defect position is moved to the viewing field of the SEM 5, and reviewing is carried out (S1308). At this moment, information reviewed is sent to the control system 8. Next, when it is not necessary to review other defect (S1309-No), the reviewing ends (S1310), and when it is necessary to review other defect (S1309-Yes), position information of the defect to be reviewed is acquired (S1311), and the procedure goes back to the sequence (S1302) to move the defect to the OM 6 mentioned above and the process is carried out. Meanwhile, if the defect cannot be detected in the defect detection sequence mentioned above (S1305-No), since the defect position may be displaced to the out of the viewing field, the portion around the viewing field of the OM 6 may be searched. When the portion around the viewing field is searched (S1312-Yes), the sample 1 is moved by the size corresponding to the viewing field (S1313), and the processes from the abovementioned defect searching sequence (S1304) are carried out. And, when the portion around the viewing field is not searched (S1312-No), the process is carried out according to the sequence (S1309).

Figure 10:
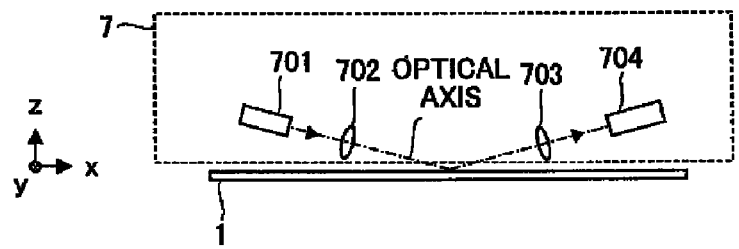
FIG. 10 is a detail view showing a height detecting system in the first embodiment of the present invention.

Next, the method of calculating the Z-position is explained with reference to FIG. 10. FIG. 10 shows the structure of the height detecting system 7, which comprising an illumination light source 701, an illumination light focusing lens 702, a detection light focusing lens 703, and a detector 704. In further detail, the illumination light source 701 is, for example, a laser oscillator or a lamp house, and the detector 704 is, for example, a CCD camera or a CCD linear sensor.

Operations of the height detecting system 7 are explained. Light emitted from the illumination light source 701 is collected onto the sample 1 by the illumination light focusing lens 702. In the sample 1, light is reflected in the direction corresponding to the incident angle to the sample 1. The reflection light is collected to the detector 704 via the detection light focusing lens 703. As the method of calculating the Z-position, first, the light detection position of the detector 704 at the reference height of the sample 1 is memorized. Next, when the height of the sample 1 changes, the light detection position in the detector 704 moves, and accordingly, by previously measuring the relation between the movement amount of the light detection position (number of pixels of the detector 704) and the change amount of the height of the sample 1, it is possible to calculate the height from the movement amount.

Meanwhile, in the case where laser light is used for illumination, since the light collecting efficiency is good, there is an advantage that a highly precise detection is feasible by use of a light source of low output. Further in the case where lamp light (=light of multiple wavelength) is used, there is an advantage that stable detection is feasible even on a sample where a transparent film is applied to the most upper surface of the sample 1. This is by averaging effect to fluctuation of film thickness.

Figure 11A:
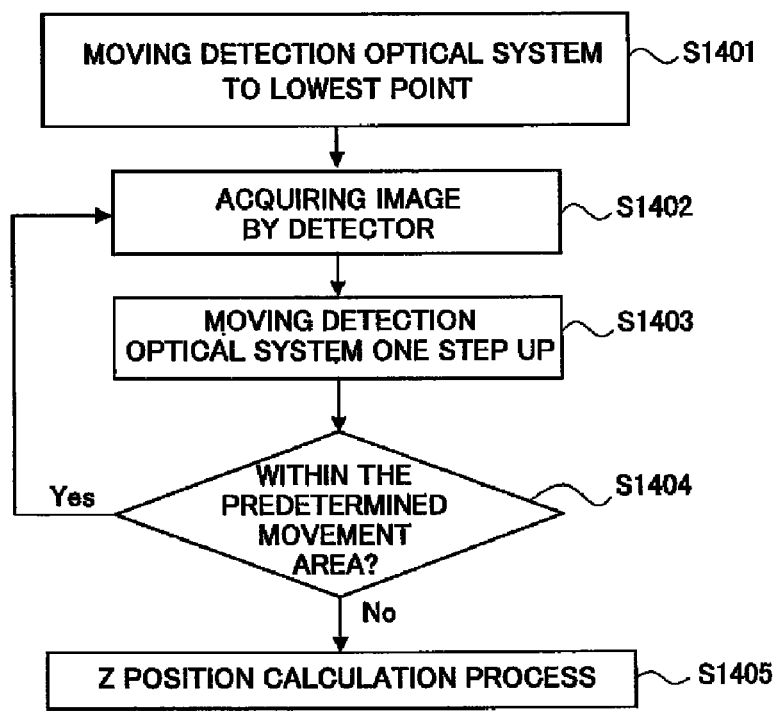
FIG. 11A is a view showing a Z-position calculation sequence in the first embodiment of the present invention.
Figure 11B:
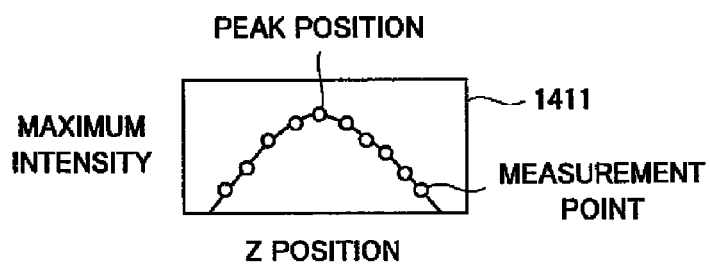
FIG. 11B is a view showing an example of a Z-position calculating process.

Another method of calculating the Z-position is explained with reference to FIG. 11. FIG. 11 shows a Z-position calculation sequence. This method is an example using images acquired by the OM 6. First, by use of the Z-movement mechanism 613, the detection optical system 605 is moved to the lowest point (=a point closest to the sample) (S1401). Next, an image is acquired by the detector 610, and sent to the control system 8 (S1402). At this moment, in the case where an image of the edge of the sample is used or the case of a sample where circuit patterns are formed, it is preferable to use the light-field detection method, and in the case of a sample without circuit patterns, it is preferable to use the dark-field detection method. After the image is acquired, the detection optical system 605 is moved one step up by the Z-movement mechanism 613 (S1403). Herein, one step means the unit of resolution for detecting the Z-position, and equal to the ½ of the focus depth of the OM 6 or less is generally preferable. After the detection optical system 605 is moved, if the position of the detection optical system 605 is in the predetermined movement area (S1404-Yes), then image is acquired again (S1402). On the other hand, if the position of the detection optical system 605 exceeds the movement area (S1404-No), the procedure goes to the sequence of the Z-position calculation process (S1405).

An example of the Z-position calculating process is explained. First, the maximum intensity in the image is searched for, and a graph 1411 where the Z-position and the maximum intensity are plotted on is created. Next, the peak position in the graph 1411 is calculated. At this moment, it is preferable to approximate it by a multidimensional curve on the basis of measurement point, and calculate the peak position. And, the Z-position corresponding to the peak position becomes the position to which the detection optical system should be moved.

Meanwhile, in the example using the abovementioned height detecting system 7, the height detecting system 7 is positioned at the position of the SEM 5, and the height of the OM 6 is determined from the height of the sample 1 at the position of the SEM 5. However, the height detection system 7 may be set at the position of the OM 6, further, it may be set at the positions of both the SEM 5 and the OM 6. When the number of the height detecting systems 7 is small, it is possible to manufacture an inexpensive apparatus, meanwhile, when height detecting systems 7 are set at both, it is possible to improve the focusing precision.

Figures 12, 13:
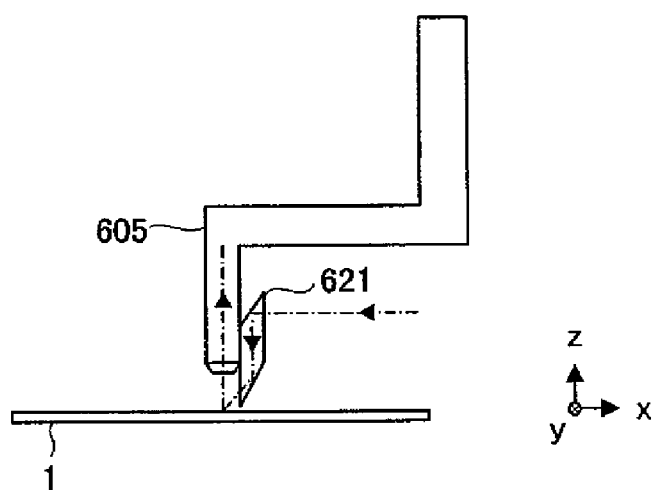
FIG. 12 is a view showing divisions of automatic defect classification in the first embodiment of the present invention.
FIG. 13 is a detail view showing another example of a rhombic illumination mirror in the first embodiment of the present invention.

Next, an example of automatic defect classification is explained with reference to FIG. 12. FIG. 12 shows combinations of the defect detection results in the OM 6 and the defect detection results in the SEM 5. In general, in the case where an optically transparent film is formed on the most upper surface of sample, defect under the film can be detected optically, but its detection is difficult by the SEM. This is because the SEM detects secondary electron and reflection electron emitted from the sample surface. By use of this nature, classified defects in FIG. 12 are obtained. That is, those defects that can be detected by the OM 6 and also by the SEM 5 are classified as defects existing on the sample surface, those defects that can be detected by the OM 6 and but not by the SEM 5 are classified as defects existing in the film or under the film. Further, those defects that cannot be detected by the OM 6 nor the SEM 5 are classified as nuisances of the defect inspection system, that is, error detection.

In the example explained above, to each defect, the correction amount of the defect position is calculated, and at every time, reviewing is made by the SEM 5, but it may be applied to the case where a plurality of defect position correction amounts are registered by the OM 6, and after the correction amounts of a plurality of defects or all the defects are calculated, reviewing is made by the SEM 5. Further, in the case where the displacement amount of defect detected by the defect inspection system is considered to be only a parallel movement amount in a fixed direction and a rotation component in a fixed direction, a correction equation of positions of all the defects is created from position correction amounts of several (3 points or more) defects, and without using reviewing by the OM 6 but using the calculated positions by the correction equation, reviewing may be made by the SEM 5. And in the case where there exists an already reviewed defect at the vicinity of defect of the object to be reviewed, the position correction amount of the reviewed defect may be applied as the position correction amount of the defect of the object to be reviewed. Further, with the correction equation as initial data, correction equation may be corrected and used at every time of coordinate correction by the OM 6. Further, in the case where the displacement amount of defect position detected by the defect inspection system is estimated to be nearly same value irrespective of sample, by use of the correction equation of already measured sample, the position of a new sample may be corrected. An advantage of reducing the number of defects whose correction amounts are calculated as above is that the throughput of reviewing work can be improved.

Further, in the case where a beam diameter of beam emitted from the dark-field illuminating unit 601 is large, and the illumination area is sufficiently large to the viewing field area, or in the case where the angle of rhombic illumination by the integrated rhombic mirror 604 is small, in the place of the epi-mirror 603 and the integrated rhombic mirror 604, an integrated prism 621 as shown in FIG. 13 may be employed. This integrated prism 621 reflects incoming light to the sample 1 side, and further rhombically illuminates the sample 1. An advantage of using such an integrated prism 621 is that it is possible to make the structure simpler than in the case where the epi-mirror 603 and the integrated rhombic mirror 604 are employed.

Furthermore, in the present embodiment, the case where reviewing is made mainly by use of an electron microscope has been explained, however, besides the electron microscope, the present invention may be applied to an X-ray analyzer or an analyzer using FIB (Focused Ion Beam) and the like, which can make more detailed reviewing than optical type.

Second Embodiment

Figure 14:
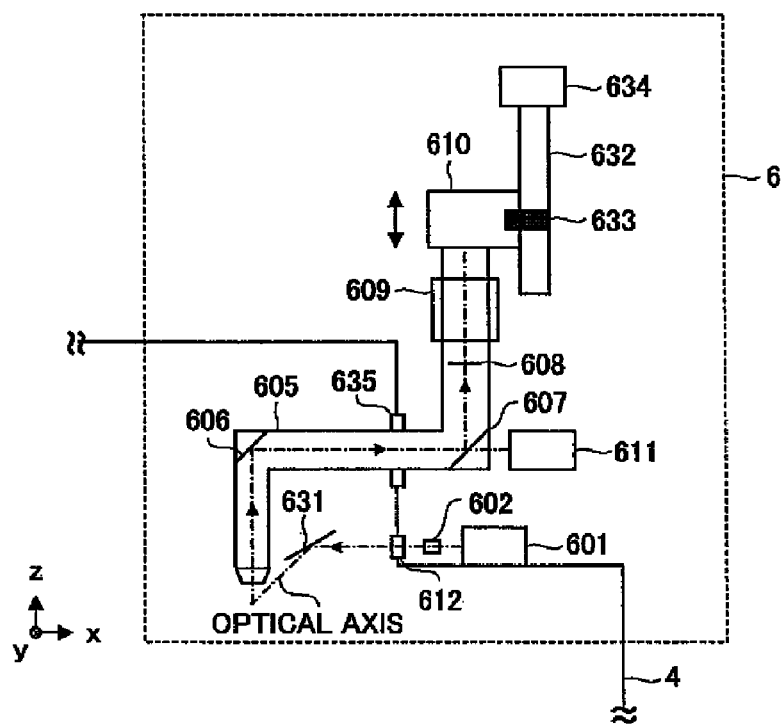
FIG. 14 is a detail view showing another example of an optical microscope in a defect reviewing apparatus according to a second embodiment.

With reference to FIG. 14, a defect reviewing method and an example of an apparatus thereof according to a second embodiment of the present invention are explained hereinafter.

In the defect reviewing apparatus according to the present embodiment, another example of the OM 6 is explained with reference to FIG. 14. The OM 6 comprises a dark-field illuminating unit 601, a coherency reducing unit 602, an epi-mirror 631, a detection optical system 605, a mirror 606, a half mirror 607, an optical filter 608, a zoom lens 609, a detector 610, a light-field illuminating unit 611, a vacuum shutout glass 612, a guide rail 632 for moving the detector 610, a origin sensor for calculate the position of the detector 610, a pulse motor 634 for moving the detector 610, a vacuum shutout glass 635, and lenses not illustrated therein. Meanwhile, the epi-mirror 631 is not necessary to move along the height change of a sample 1, therefore, it may be fixed onto the detection optical system 605.

In the abovementioned first embodiment, structural components accompanying the detection optical system 605 are moved in the Z-direction and thereby focusing is carried out. However, in the present embodiment, the detection optical system 605 is fixed, and the detector 610 is moved in the Z-direction and thereby focusing is carried out. The structure according to the present embodiment does not require to move the detection optical system 605, therefore there is an advantage that the structure of the Z-movement mechanism is made simple. However, since the image providing magnification to the detector 610 fluctuates, if the magnification fluctuation becomes a problem, it is necessary to correct the magnification and the like.

Operations in the structure of the defect reviewing apparatus including the OM 6 shown in FIG. 14 are explained. The operations to acquire images by the light-field detection method and the dark-field detection method are same as those in the abovementioned first embodiment. Therefore, herein, a method of focusing and a method of correcting magnification are described.

First, as a method of measuring the height of the sample 1, the abovementioned height detecting system 7 may be employed. At this moment, if the distance between the sample 1 and a main flat surface on the object side of the detection optical system 605 is defined as "a", and the distance between a main flat surface on the image side of the detection optical system 605 and the light receiving surface of the detector 610 is defined as "b", and the focus distance of the detection optical system 605 is defined as 'f'. From the information acquired from the abovementioned height detection system 7, the "a" is already known, and the focus distance 'f' is also already known, therefore from the relation equation of (Equation 1), the value of "b" can be calculated. Accordingly, when the detector 610 is moved to the position to become the distance of "b", focus adjusting is completed.

$$1/a + 1/b = 1/f \qquad \text{(Equation 1)}$$

The method of moving the detector 610 is, for example, the method of moving it by use of the pulse motor 634 along the guide rail 632 in the Z-direction. As for the movement amount by the pulse motor 634, the number of pulses from an origin sensor 633 may be calculated. At this moment, image providing magnification "M" becomes as shown in (Equation 2). And when the magnification at the reference position is defined as M0, the value "k" to be calculated by (Equation 3) becomes the magnification fluctuation amount. Accordingly, by multiplying the displacement amount of the defect position calculated from image by the magnification fluctuation amount "k", it is possible to calculate the position correction amount after magnification correction.

$$M = b/a \qquad \text{(Equation 2)}$$

$$k = M/M0 \qquad \text{(Equation 3)}$$

Meanwhile, in the case when the height detecting system 7 is not used, in place of image acquisition by moving the detection optical system 605 explained in the abovedescribed first embodiment, by moving the detector 610 to acquire image, focus adjusting made from detected image is feasible. In this case, the position of the detector 610 is calculated by the number of pulses from the origin sensor 633, and the calculated value is substituted to the value of the abovementioned "b" and the magnification "M" is calculated.

Third Embodiment

Figure 15:
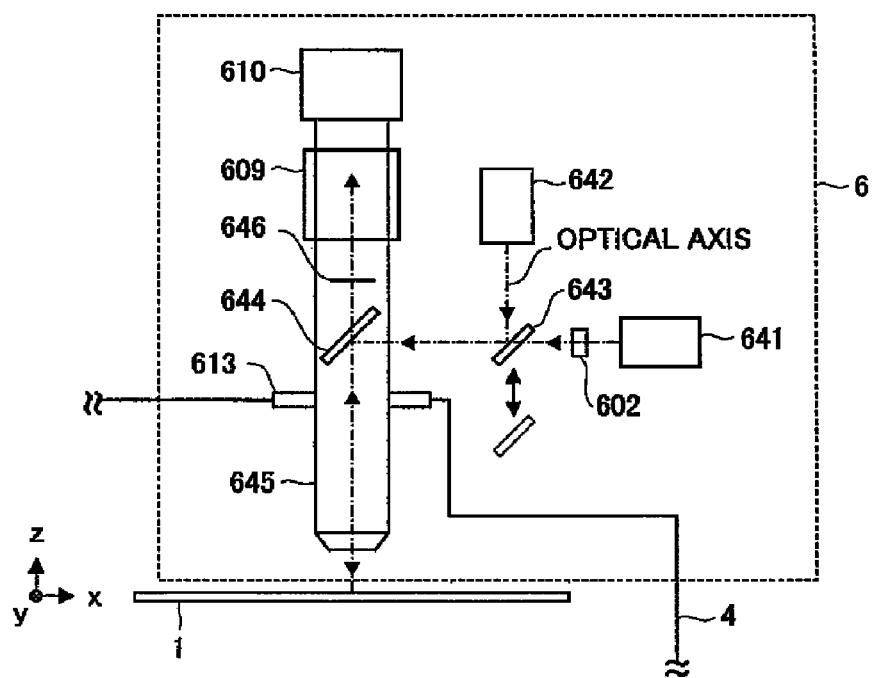
FIG. 15 is a detail view showing another example of an optical microscope in a defect reviewing apparatus according to a third embodiment.

With reference to FIG. 15 and FIG. 16, a defect reviewing method and an example of an apparatus thereof according to a third embodiment of the present invention are explained hereinafter.

In the defect reviewing apparatus according to the present embodiment another example of the OM 6 is described with reference to FIG. 15. The OM 6 comprises a laser illuminating unit 641, a coherency reducing unit 602, a lamp illuminating unit 642, a mirror 643, a half mirror 644, a detection optical system 645, an optical filter 646, a zoom lens 609, a detector 610, a Z-movement mechanism 613, and lenses not illustrated therein. The present embodiment is an example where only epi-illumination is arranged as illumination light path, and has an advantage that the structure can be made simple.

Operations in the structure of the defect reviewing apparatus including the OM 6 shown in FIG. 15 are explained. First, the method of acquiring a dark-field image by laser light is explained. At the moment of laser illumination, the mirror 643 is excluded from the laser illumination light path by use of a mechanism not illustrated therein. Light emitted from the laser illuminating unit 641 goes through the coherency reducing unit 602 and is reflected to the sample 1 side by the half mirror 644 arranged in the detection optical system 645, and radiated onto the sample 1. Reflection light and scattered light from the sample 1 are detected by the detection optical system 645, and the light passing the optical filter 646 provides an image onto the detector 610 by the zoom lens 609.

Figure 16B:
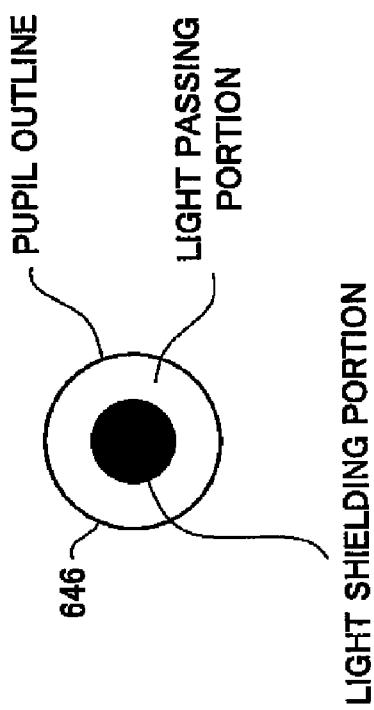
FIG. 16B is a detail top view showing an optical filter in the defect reviewing apparatus according to the third embodiment.
Figure 16A:
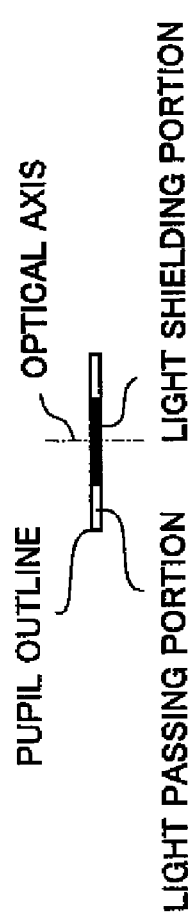
FIG. 16A is a detail cross sectional view showing an optical filter in a defect reviewing apparatus according to a third embodiment.

Here, the optical filter 646 is set at the pupil position of the detection optical system 645, and is a filter of the shape shown in FIG. 16. FIG. 16A is a cross sectional view of the optical filter 646, and FIG. 16B is a top view thereof. The optical filter 646 is a filter that has a light shielding portion at the portion around the optical axis thereof, and let the light positioned between the light shielding portion and the pupil outline pass through. The light shielding portion is set at the area that shields the normal reflection light of the sample 1. Further, the light transmitting portion is a glass plate or a polarization plate. When the light transmitting portion is a glass plate, normal dark-field detection is available, and when the light transmitting portion is a polarization plate, dark-field polarization detection is available.

Further, when light-field detection is carried out, the optical filter 646 may be excluded from the light path by a mechanism not illustrated therein. Further, when reviewing is performed by lamp illumination, the mirror 643 may be inserted into the light path, and the light emitted from the lamp illuminating unit 642 may be reflected by the mirror 643 for use.

Fourth Embodiment

Figure 17:
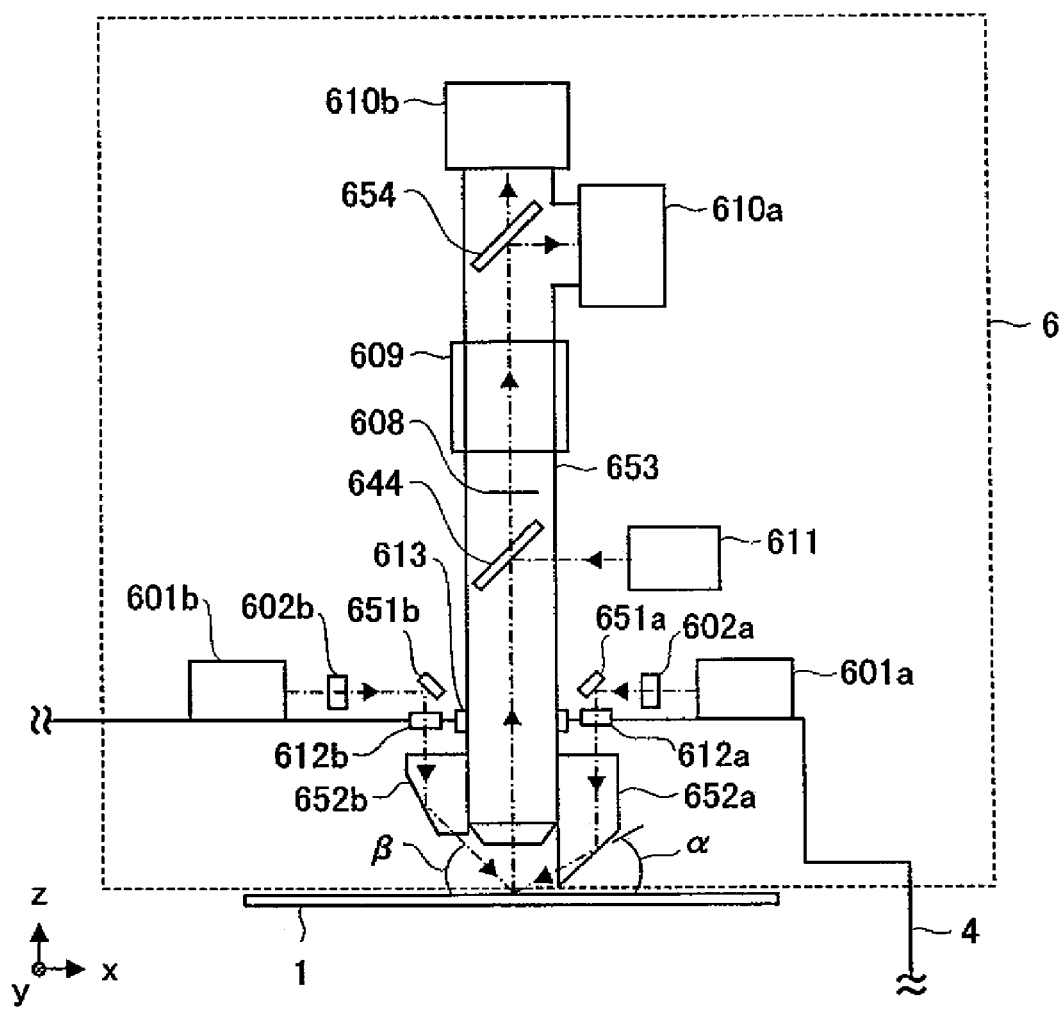
FIG. 17 is a detail view showing another example of an optical microscope in a defect reviewing apparatus according to a fourth embodiment.

With reference to FIG. 17, a defect reviewing method and an example of an apparatus thereof according to a fourth embodiment of the present invention are explained hereinafter.

In the defect reviewing apparatus according to the present embodiment, still another example of the OM 6 is explained with reference to FIG. 17. The OM 6 herein comprises dark-field illuminating units 601a and 601b, coherency reducing units 602a and 602b, mirrors 651 and 651b, vacuum shutout glasses 612a and 612b, integrated rhombic mirrors 652a and 652b, a detection optical system 653, a half mirror 644, an optical filter 608, a zoom lens 609, a dichroic mirror 654, detectors 610a and 610b, a light-field illuminating unit 611, a Z-movement mechanism 613, and lenses not illustrated therein.

Here, subscripts "a" and "b" in the present embodiment show parts that correspond to different wavelengths. That is, the dark-field illuminating units 601a and 601b radiate lights of different wavelengths respectively. For example, the dark-field illuminating unit 601a radiates laser light of wavelength 532 nm, and the dark-field illuminating unit 601b radiates laser light of wavelength 405 nm, and not limited to the abovementioned wavelengths, but a combination of other wavelengths may be used. The dichroic mirror 654 has the performance to separate the different wavelengths. Further, the integrated rhombic mirrors 652a and 652b have structures where radiation angles to the sample 1 are different. That is, the integrated rhombic mirror 652a radiates light to the sample 1 at angle $\alpha$, and the integrated rhombic mirror 652b radiates light to the sample 1 at angle $\beta$, and, $\alpha$ and $\beta$ are different angles. Further, the integrated rhombic mirrors 652a and 652b are arranged in the detection optical system 653. And, according to the movement of the detection optical system 653 in the Z-direction, the integrated rhombic mirrors 652a and 652b move. The present embodiment is an example to be used in the case when there are differences in defect detecting performance due to differences in illumination angles.

Operations in the structure of the defect reviewing apparatus including the OM 6 shown in FIG. 17 are explained. The light-field detection method and the height detection method are same as those in the abovementioned third embodiment. Therefore, here, a dark-field detection method is explained.

Lights emitted from the dark-field illuminating units 601a and 601b respectively pass the coherency reducing units 602a and 602b, and are reflected to the sample 1 side by the mirrors 651a and 651b. The reflected lights are radiated onto the sample 1 by the integrated rhombic mirrors 652a and 652b. The lights reflected and scattered from the sample 1 are collected by the detection optical system 653, and the light passing the optical filter 608 provides an image on the detectors 610a and 610b by the zoom lens 609. At this moment, wavelengths are separated by the dichroic mirror 654, and the reflected and scattered lights by the lights radiated at the different illumination angles are detected by the respectively different detectors 610a and 610b. Signals obtained by the detectors 610a and 601b are sent to the control system 8 where the defect detection process is carried out.

Meanwhile, the present embodiment was explained with the example where defect detections by different illumination angles are carried out simultaneously. However, when there is room in defect detection time, detections may be carried out by changing illumination angles in series. In this case, only one set of the detector 610 may work. Further, in the present embodiment, the example where two kinds of illumination angles are used was explained. However, the number of kinds of the illumination angles may be increased as necessity.

In the foregoing, the invention made by the inventors of the present invention has been concretely described based on the embodiments. However, it is needless to say that the present invention is not limited to the foregoing embodiments and various modifications and alterations can be made within the scope of the present invention.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method of inspecting defects of a sample, the method comprising the steps of:
    a first step for, on a basis of position information of defects on a sample placed on a table that is movable in an X-Y plane in which the position information of defects is previously detected and obtained by inspecting the sample by an other inspection system, driving the table and making the defects come into a viewing field of an optical microscope, and adjusting focus of the optical microscope onto the sample;
    a second step for re-detecting the defects, based on the position information, by the optical microscope to obtain a first detection result;
    a third step for correcting displacement amounts of the position information of defects on a basis of position information of defects re-detected from the first detection result obtained at the second step; and
    a fourth step for reviewing the defects, whose position information is corrected at the third step, by an electron microscope to obtain a second detection result;
    wherein types of defects are classified based upon defects on a surface and inside the sample being detected by the first detection result and defects on the surface of the sample being detected by the second detection result.

2. The method of inspecting defects of a sample according to claim 1,
    wherein the classification classifies whether the defects on the sample are defects of the uppermost surface of the sample when the defects are detected by both the first detection result and the second detection result or defects of a lower layer of the sample when the defects are detected by the first detection result but not the second detection result.

3. The method of inspecting defects of a sample according to claim 2,
    wherein the classification classifies that pseudo defects are obtained when the defects are not detected by either the first detection result or the second detection result.

4. The method of inspecting defects of a sample according to claim 1,
    wherein the classification classifies that pseudo defects are obtained when the defects are not detected by either the first detection result or the second detection result.

5. The method of inspecting defects of a sample according to claim 1,
    wherein the types of defects are classified according to whether the defects are detected by both of the first detection result and the second detection result or detected by only the first detection result.

6. The method of inspecting defects of a sample according to claim 1,
    wherein the types of defects are classified according to whether the defects are detected by both of the first detection result and the second detection result, or detected by only the first detection result, or detected by neither the first detection result nor the second detection result.

7. The method of inspecting defects of a sample according to claim 1,
    wherein the types of defects pertain to whether the defect is a defect on a surface or a defect inside the sample.

* * * * *